US00RE46629E

(19) United States
(12) Reissued Patent
Alken

(10) Patent Number: US RE46,629 E
(45) Date of Reissued Patent: Dec. 12, 2017

(54) DEUTERATED CATECHOLAMINE DERIVATIVES AND MEDICAMENTS COMPROMISING SAID COMPOUNDS

(71) Applicant: Teva Pharmaceuticals International GmbH, Jona (CH)

(72) Inventor: Rudolf-Giesbert Alken, Neuenhagen (DE)

(73) Assignee: Teva Pharmaceuticals International GmbH, Jona (CH)

(21) Appl. No.: 14/464,444

(22) Filed: Aug. 20, 2014

Related U.S. Patent Documents

Reissue of:
(64) Patent No.: 8,168,820
Issued: May 1, 2012
Appl. No.: 10/539,845
PCT Filed: Dec. 18, 2003
PCT No.: PCT/DE03/04203
§ 371 (c)(1),
(2) Date: Feb. 9, 2006
PCT Pub. No.: WO2004/056724
PCT Pub. Date: Jul. 8, 2004

(30) Foreign Application Priority Data

Dec. 19, 2002 (DE) ..... 102 61 807

(51) Int. Cl.
*C07B 59/00* (2006.01)
*C07C 229/08* (2006.01)
*A61P 25/00* (2006.01)
*A61K 31/198* (2006.01)
*C07C 229/36* (2006.01)

(52) U.S. Cl.
CPC ..... *C07C 229/36* (2013.01); *C07B 59/001* (2013.01)

(58) Field of Classification Search
CPC .. C07C 229/36; C07B 59/001; C07B 2200/07
USPC ..... 562/446; 560/37, 38, 39, 40
See application file for complete search history.

(56) References Cited

U.S. PATENT DOCUMENTS

| | | | | |
|---|---|---|---|---|
| 3,699,158 | A * | 10/1972 | Putter | 562/445 |
| 3,769,424 | A | 10/1973 | Bayne | |
| 4,663,349 | A | 5/1987 | Repta | |
| 4,962,223 | A | 10/1990 | Cannata | |
| 5,017,607 | A * | 5/1991 | Chiesi | 514/534 |
| 5,525,631 | A * | 6/1996 | Milman et al. | 514/567 |
| 6,221,335 | B1 * | 4/2001 | Foster | 424/1.81 |
| 6,440,710 | B1 * | 8/2002 | Keinan et al. | 435/148 |
| 6,603,008 | B1 * | 8/2003 | Ando et al. | 546/269.7 |
| 6,693,008 | B1 | 2/2004 | Sato et al. | |

FOREIGN PATENT DOCUMENTS

| | | |
|---|---|---|
| DE | 2 049 115 A | 4/1972 |
| DE | 2049115 A1 | 4/1972 |
| DE | 10261807 A1 | 7/2004 |
| EP | 0 357 565 A2 | 3/1990 |
| EP | 0357565 A2 | 3/1990 |
| JP | S63-27428 | 6/1988 |
| JP | H07-285860 | 10/1995 |
| JP | 2002/097137 | 4/2002 |
| WO | WO 99/18120 | 4/1999 |
| WO | WO 00/48610 | 8/2000 |
| WO | WO 02/088100 | 11/2002 |

OTHER PUBLICATIONS

Bennett, et al., "Deuteriation and tritiation of aryl aldehydes in the formyl group and the synthesis of (±)-3,4-dihydroxy[-2H2]phenylalanine", J. Chem. Soc. C, 1970, 2049-2051.
Binns, et al., Studies related to the chemistry of melanins. Part VIII. The pyrrolecarboxylic acids formed by oxidation or hydrolysis of melanins derived from 3,4-dihydroxyphenethylamine or (±)-3,4-dihydroxyphenylalanine. J. Chem. Soc. C, 1128,1979.
Dewar et al., Neuro-Psychopharmacology & Biological Psychiatry, 1985, 9(5-6), 675-680.
Dyck et al., "Effects of Deuterium Substitution on the Catabolism of β-Phenylethylamine: An In Vivo Study", Journal of Neurochemistry, vol. 46, Issue 2, pp. 399-404, Feb. 1986.
Gouyette, A., "Synthesis of Deuterium-Labelled Elliptinium and its Use in Metabolic Studies", Biomedical & Environmental Mass Spectrometry, vol. 15, Issue 5, pp. 243-247, Mar. 1988.
Haskins, Biomedical Spectrometry vol. 9 Issue 7, pp. 269-277, 1982.
Ogura, et al., "Clinical effect of L-dopa on Schizophrenia", Curr Ther Res Clin Exp. 1976, 20(3):308-18.
Tonn et al., "Simultaneous analysis of diphenhydramine and a stable isotope analog (2H10)diphenhydramine using capillary gas chromatography with mass selective detection in biological fluids from chronically instrumented pregnant ewest†", Biological Mass Spectrometry, vol. 22, Issue 11, pp. 633-642, 1993.
Weiner et al., Neurology, 2000, 54(7), p. 1538.
Wolen, "The Application of Stable Isotopes to Studies of Drug Bioavailability and Bioequivalence", The Journal of Clinical Pharmacology, vol. 26, Issue 6, pp. 419-424, Jul.-Aug. 1986.
Milstien et al.,"Studies on the phenylalanine hydroxylase system in vivo. An in vivo assay based on the liberation of deuterium or tritium into the body water from ring-labeled L-phenylalanine", Journal of Biochemistry, vol. 250 pp. 4782-4785, 1975.
Chen et al. Biotechnology Letters, vol. 14, No. 4, pp. 269-274, 1992.
Sourkes et al., "Comparative Metabolism of d- and I-3,4-dihydroxyphenylaline in Normal and Pyridoxine-Deficient Rats", Biochem J. Dec. 1964; 93(3): 469-474.
Hayashi et al., "Analysis of L-DOPA in vivo Kinetics by the Stable Isotope Tracer Method", Proceedings of Japanese Society for Biomedical Mass Spectrometry, 13, (9) 1988, 229-232.

(Continued)

*Primary Examiner* — Dwayne Jones
(74) *Attorney, Agent, or Firm* — Baker & Hostetler LLP

(57) ABSTRACT

The present invention concerns deuterated catecholamine derivatives as well as pharmaceuticals containing these compounds. In addition, the invention concerns the use of deuterated catecholamine derivatives as well as physiologically compatible salts thereof, and also pharmaceutical compositions, which contain these compounds, also in combination with enzyme inhibitors, for the treatment of dopamine deficiency diseases or diseases which are based on disrupted tyrosine transport or disrupted tyrosine decarboxylase, as well as other disorders.

21 Claims, No Drawings

(56) References Cited

OTHER PUBLICATIONS

"Amphetamine Adducts of Melanin Intermediates Demonstrated by Matrix-Assisted Laser Desorption/Ionization Time-of-Flight Mass Spectrometry" David J. Claffey and James A. Ruth Chem. Res. Toxicol., 2001, 14 (9), pp. 1339-1344.

"Changes in Brain Catecholamine Levels Following DL-Dopa are not Potentiated by Deuterium Substitution" Dewar KM, Dyck LE, Durden DA, Boulton AA., Prog Neuropsychopharmacol Biol Psychiatry. 1985;9(5-6):675-80.

"Conversion of 3,4-Dihydroxyphenylalanine and Deuterated 3,4-Dihydroxyphenylalanine to Alcoholic Metabolites of Catecholamines in Rat Brain," Edwards DJ, Rizk M. J Neurochem. May 1981;36(5):1641-7.

"Pharmacological uses and perspectives of heavy water and deuterated compounds," Kushner DJ, Baker A, Dunstall TG. Can J Physiol Pharmacol. Feb. 1999;77(2):79-88.

"Quantitative analysis of N-phenylpropenoyl-L-amino acids in roasted coffee and cocoa powder by means of a stable isotope dilution assay" Stark T, Justus H, Hofmann T. J Agric Food Chem. Apr. 19, 2006;54(8):2859-67.

"Deuterium exchange labelling of biologically important phenols, indoles and steroids" R. F. Vining, G. A. Smythe and M. A. Long Journal of Labelled Compounds and Radiopharmaceuticals vol. 18, Issue 11, pp. 1683-1692, Nov. 1981.

"Three types of stereospecificity and the kinetic deuterium isotope effect in the oxidative deamination of dopamine as catalyzed by different amine oxidases" Peter H. Yu Biochemistry and Cell Biology, 1988, 66(8): 853-861.

"Stereospecific Deuterium Substitution at the alpha-Carbon Position of Dopamine and its Effect on Oxidative Deamination Catalyzed by MAO-A and MAO-B from Different Tissues," Yu PH, Bailey BA, Durden DA, Boulton AA. Biochem Pharmacol. Mar. 15, 1986;35(6):1027-36.

Oba et al. "Stereo-divergent Synthesis of L-threo- and L-erythro-[2,3-$^{2}H_{2}$] amino acids using optically active dioxopiperazine as a chiral template" J. Chem. Soc., Perkin Trans. 1, Jan. 1998.

Binns et al. "Studies related to . . . " J. Chem Soc., 2049-51 (1970).

* cited by examiner

DEUTERATED CATECHOLAMINE DERIVATIVES AND MEDICAMENTS COMPROMISING SAID COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The invention concerns deuterated catecholamine derivatives as well as pharmaceuticals containing these compounds.

Known representatives of catecholamines, such as L-dopa (levodopa) as well as their carboxylic acid esters, are utilized, among other things, for the treatment of Parkinson's disease and restless leg syndrome. Such a pharmaceutical which contains levodopa is, for example, Dopaflex®. L-dopa acts on the dopamine concentration in neurons of the brain. Unlike dopamine itself, it can pass through the blood-brain barrier and is converted to dopamine in the brain.

In addition, levodopa is administered in combination with active additives in pharmaceuticals. Combinations of levodopa are used with peripheral decarboxylase inhibitors, with inhibitors of the enzyme catechol-O-methyltransferase (COMT), with inhibitors of the enzyme monoamine oxidase (MAO) and with dopamine β-hydroxylase inhibitors.

In this connection, the decarboxylase inhibitors used are, for example: D,L-serine 2-(2,3,4-trihydroxybenzyl) hydrazide (benserazide), (−)-L-α-hydrazino-3,4-dihydroxy-α-methylhydrocinnamic acid (carbidopa), L-serine-2-(2,3,4-trihydroxybenzyl) hydrazide, glycine-2-(2,3,4-trihydroxybenzyl) hydrazide and L-tyrosine-2-(2,3,4-trihydroxybenzyl) hydrazide. Examples of combination preparations of levodopa and decarboxylase inhibitors include, among others: Madopar® (levodopa and benserazide hydrochloride) as well as Nacome® (levodopa and carbidopa).

Examples of COMT inhibitors are entacapone (Comtan®) and cabergoline and frequently used MAO inhibitors are selegiline hydrochloride, moclobemide and tranylcypromine.

Calcium 5-butyl picolinate and calcium 5-pentyl picolinate are described as inhibitors for dopamine-β-hydroxylase (DE 2,049,115).

An object of the present invention is to prepare deuterated catecholamine derivatives, which have improved pharmacokinetic and/or pharmacodynamic properties when compared to compounds already known, as well as to prepare catecholamine derivatives, which can be utilized for the prophylaxis of psychoses including schizophrenia, and which can be used for producing pharmaceuticals for the prophylaxis of psychoses.

It has been surprisingly found that the deuterated catecholamine derivatives according to the invention have substantially better pharmacokinetic and/or pharmacodynamic properties than the undeuterated compounds and that they can also be utilized for the prophylaxis of psychoses and can be used for producing pharmaceuticals for the prophylaxis of psychoses.

According to the invention, the object is thus solved by the preparation of compounds of general formula I:

Formula I

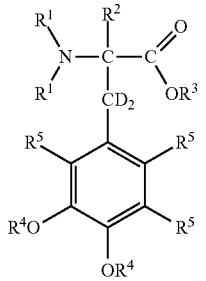

wherein $R^1$ is H or D, $R^2$ indicates H or D, $R^3$ is H, D, $C_1$-$C_6$ alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is H or D.

Preferred are deuterated catecholamine derivatives according to the general formula I, wherein $R^1$ is H or D, $R^2$ indicates H or D, $R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is D.

Particularly preferred are deuterated catecholamine derivatives according to the general formula I, wherein $R^1$ is H or D, $R^2$ indicates H or D, $R^3$ is D, $C_1$ to $C_6$-alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is D.

Additionally preferred are deuterated catecholamine derivatives according to the general formula I, wherein $R^1$ is H or D, $R^2$ indicates D, $R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is D.

Particularly advantageous are deuterated catecholamine derivatives according to the general formula I, wherein $R^1$ is H or D, $R^2$ indicates D, $R^3$ is $C_1$ to $C_6$-alkyl or $C_5$ to $C_6$-cycloalkyl, $R^4$ indicates H or D and $R^5$ is D.

Additionally advantageous are deuterated catecholamine derivatives according to the general formula I, wherein $R^1$ is H or D, $R^2$ indicates D, $R^3$ is methyl, $R^4$ indicates H or D and $R^5$ is D.

Particularly advantageous are deuterated catecholamine derivatives according to the general formula I, wherein $R^1$ is H or D, $R^2$ indicates D, $R^3$ is ethyl, $R^4$ indicates H or D and $R^5$ is D.

Preferred are deuterated catecholamine derivatives according to the general formula I, wherein $R^1$ is H or D, $R^2$ indicates D, $R^3$ is perdeuteroethyl, $R^4$ indicates H or D and $R^5$ is D.

Additionally preferred are deuterated catecholamine derivatives according to the general formula I, wherein $R^1$ is H or D, $R^2$ indicates H or D, $R^3$ is perdeuteroethyl, $R^4$ indicates H or D and $R^5$ is D.

Additionally preferred are deuterated catecholamine derivatives according to the general formula I, wherein $R^1$ is H or D, $R^2$ indicates H or D, $R^3$ is perdeuteroethyl, $R^4$ indicates D and $R^5$ is H or D.

Particularly preferred are the following deuterated catecholamine derivatives according to the general formula I:

L-2-amino-3,3-dideutero-3-(3,4-dihydroxyphenyl) propionic acid,

L-2-amino-3,3-dideutero-3-(3,4-dihydroxyphenyl) methyl propionate,

L-2-amino-3,3-dideutero-3-(3,4-dihydroxyphenyl) ethyl propionate,

L-2-amino-3,3-dideutero-3-(3,4-dihydroxyphenyl) cyclohexyl propionate,

L-2-amino-3,3-dideutero-3-(3,4-dihydroxyphenyl) perdeuteromethyl propionate,
L-2-amino-3,3-dideutero-3-(3,4-dihydroxyphenyl) perdeuteroethyl propionate,
L-2-amino-3,3-dideutero-3-(3,4-dihydroxyphenyl) perdeuterocyclohexyl propionate,
L-2-amino-2,3,3-trideutero-3-(3,4-dihydroxyphenyl) propionic acid,
L-2-amino-2,3,3-trideutero-3-(3,4-dihydroxyphenyl) methyl propionate,
L-2-amino-2,3,3-trideutero-3-(3,4-dihydroxyphenyl) ethyl propionate,
L-2-amino-2,3,3-trideutero-3-(3,4-dihydroxyphenyl) cyclohexyl propionate,
L-2-amino-2,3,3-trideutero-3-(3,4-dihydroxyphenyl) perdeuteromethyl propionate,
L-2-amino-2,3,3-trideutero-3-(3,4-dihydroxyphenyl) perdeuteroethyl propionate,
L-2-amino-2,3,3-trideutero-3-(3,4-dihydroxyphenyl) perdeuterocyclohexyl propionate,
L-2-amino-2,3,3-trideutero-3-(2,3,6-trideutero-4,5-dihydroxyphenyl) propionic acid,
L-2-amino-2,3,3-trideutero-3-(2,3,6-trideutero-4,5-dihydroxyphenyl) methyl propionate,
L-2-amino-2,3,3-trideutero-3-(2,3,6-trideutero-4,5-dihydroxyphenyl) ethyl propionate,
L-2-amino-2,3,3-trideutero-3-(2,3,6-trideutero-4,5-dihydroxyphenyl) cyclohexyl propionate,
L-2-amino-2,3,3-trideutero-3-(2,3,6-trideutero-4,5-dihydroxyphenyl) perdeuteromethyl propionate,
L-2-amino-2,3,3-trideutero-3-(2,3,6-trideutero-4,5-dihydroxyphenyl) perdeuteroethyl propionate,
L-2-amino-2,3,3-trideutero-3-(2,3,6-trideutero-4,5-dihydroxyphenyl) perdeuterocyclohexyl propionate,
L-2-amino-2,3,3-trideutero-3-(2,3,6-trideutero-4,5-dideuteroxyphenyl) perdeuterocyclohexyl propionate,
L-2-amino-3,3-dideutero-3-(4,5-dideuteroxyphenyl) perdeuterocyclohexyl propionate.

Another embodiment of the invention is the use of the deuterated catecholamine derivatives according to the invention as well as physiologically compatible salts thereof for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for the stimulation of the release of growth hormone, for the treatment of neurological symptoms of chronic manganese intoxications, of amyotrophic lateral sclerosis and of multiple system atrophy.

Preferred is the use of deuterated catecholamine derivatives as well as physiologically compatible salts thereof, in combination with an enzyme inhibitor or several enzyme inhibitors, for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for stimulating the release of growth hormone, for the treatment of neurological symptoms of chronic manganese intoxications, of amyotrophic lateral sclerosis and of multiple system atrophy.

It is advantageous if the enzyme inhibitor or the enzyme inhibitors involve decarboxylase inhibitors and/or catechol-O-methyltransferase inhibitors and/or monoamine oxidase inhibitors and/or β-hydroxylase inhibitors.

It is particularly advantageous if the decarboxylase inhibitor is selected from the group consisting of the following: D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically compatible salts thereof.

In particular, it is also advantageous if the catechol-O-methyltransferase inhibitor is selected from entacapone and cabergoline as well as physiologically compatible salts thereof.

It is also preferred if the monoamine oxidase inhibitor is selected from the group consisting of selegiline, moclobemide and tranylcypromine, as well as physiologically compatible salts thereof.

In addition, it is particularly preferred if the β-hydroxylase inhibitor is selected from calcium 5-butyl picolinate and calcium 5-pentyl picolinate as well as physiologically compatible salts thereof.

Another subject of the invention is the use of the deuterated catecholamines according to the invention as well as physiologically compatible salts thereof for the production of pharmaceuticals for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for stimulating the release of growth hormone, for the treatment of neurological symptoms of chronic manganese intoxications, of amyotrophic lateral sclerosis and of multiple system atrophy.

Another subject of the present invention is a pharmaceutical composition which contains the deuterated catecholamines according to the invention as well as their physiologically compatible salts for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for stimulating the release of growth hormone, for the treatment of neurological symptoms of chronic manganese intoxications, of amyotrophic lateral sclerosis and of multiple system atrophy, in addition to pharmaceutically compatible adjuvants and additives.

Particularly advantageous is a pharmaceutical composition which contains the deuterated catecholamines according to the invention as well as physiologically compatible salts thereof for the treatment of Parkinson's disease, restless leg syndrome, dystonia, for the inhibition of prolactin secretion, for stimulating of the release of growth hormone, for the treatment of neurological symptoms of chronic manganese intoxications, of amyotrophic lateral sclerosis and of multiple system atrophy, as well as one or more enzyme inhibitors, in addition to pharmaceutically compatible adjuvants and additives.

A pharmaceutical composition is particularly preferred in which the enzyme inhibitor or the enzyme inhibitors involve decarboxylase inhibitors and/or catechol-O-methyltransferase inhibitors and/or monoamine oxidase inhibitors and/or β-hydroxylase inhibitors.

Additionally preferred is a pharmaceutical composition in which the decarboxylase inhibitor is selected from the group consisting of D,L-serine 2-(2,3,4-trihydroxybenzyl) hydrazide (benserazide), (−)-L-α-hydrazino-3,4-dihydroxy-alpha-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically compatible salts thereof.

Particularly advantageous is a pharmaceutical composition in which the catechol-O-methyltransferase inhibitor is selected from entacapone and cabergoline as well as their physiologically compatible salts.

Additionally advantageous is a pharmaceutical composition in which the monoamine oxidase inhibitor is selected from the group consisting of selegiline, moclobemide and tranylcypromine as well as physiologically compatible salts thereof.

In addition, a pharmaceutical composition is preferred in which the β-hydroxylase inhibitor is selected from calcium 5-butyl picolinate and calcium 5-pentylpicolinate as well as physiologically compatible salts thereof.

Another subject of the invention is the use of the deuterated catecholamine derivatives according to the invention as well as physiologically compatible salts thereof for use in the prophylaxis of psychoses, particularly in predisposed patients, for the prophylaxis of a relapse and also particularly for the treatment of acute psychoses, for example, with negative symptomatology.

Particularly preferred is the use of the deuterated catecholamine derivatives according to the invention as well as physiologically compatible salts thereof, in combination with one or more enzyme inhibitors, for use in the prophylaxis of psychoses and for use in acute psychoses, preferably psychoses with negative symptomatology.

Particularly preferred is the use of the deuterated catecholamine derivatives according to the invention as well as physiologically compatible salts thereof, if the enzyme inhibitor or the enzyme inhibitors are decarboxylase inhibitors and/or catechol-O-methyltransferase inhibitors and/or monoamine oxidase inhibitors and/or β-hydroxylase inhibitors.

Particularly preferred is the use of the deuterated catecholamine derivatives according to the invention as well as physiologically compatible salts thereof, if the decarboxylase inhibitor is selected from the group consisting of D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically compatible salts thereof.

The use of the deuterated catecholamine derivatives according to the invention as well as physiologically compatible salts thereof is advantageous, if the catechol-O-methyltransferase inhibitor is selected from entacapone and cabergoline as well as physiologically compatible salts thereof.

In addition, the use of the deuterated catecholamine derivatives according to the invention as well as physiologically compatible salts thereof is advantageous, if the monoamine oxidase inhibitor is selected from the group consisting of selegiline, moclobemide and tranylcypromine as well as physiologically compatible salts thereof.

The use of the deuterated catecholamine derivatives according to the invention as well as physiologically compatible salts thereof is particularly advantageous, if the β-hydroxylase inhibitor is selected from calcium 5-butyl picolinate and calcium 5-pentyl picolinate as well as physiologically compatible salts thereof.

Another subject of the invention is the use of the deuterated catecholamine derivatives according to the invention as well as physiologically compatible salts thereof for the production of pharmaceuticals for use in the prophylaxis of psychoses.

Still another subject of the invention is a pharmaceutical composition which contains the deuterated catecholamines according to the invention as well as physiologically compatible salts thereof for use in the prophylaxis of psychoses and for the treatment of acute psychoses, in addition to pharmaceutically compatible adjuvants and additives.

Particularly advantageous is a pharmaceutical composition which contains the deuterated catecholamines according to the invention as well as physiologically compatible salts thereof for the prophylaxis of psychoses and for the therapy of acute psychoses as well as one or more enzyme inhibitors, in addition to pharmaceutically compatible adjuvants and additives.

Particularly preferred is a pharmaceutical composition in which the enzyme inhibitor or the enzyme inhibitors are decarboxylase inhibitors and/or catechol-O-methyltransferase inhibitors and/or monoamine oxidase inhibitors and/or β-hydroxylase inhibitors.

Additionally advantageous is a pharmaceutical composition in which the decarboxylase inhibitor is selected from the group consisting of D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically compatible salts thereof.

Particularly advantageous is a pharmaceutical composition in which the catechol-O-methyltransferase inhibitor is selected from entacapone and cabergoline as well as physiologically compatible salts thereof.

Particularly advantageous is a pharmaceutical composition in which the monoamine oxidase inhibitor is selected from the group consisting of selegiline, moclobemide and tranylcypromine as well as physiologically compatible salts thereof.

Particularly preferred is a pharmaceutical composition in which the β-hydroxylase inhibitor is selected from calcium 5-butyl picolinate and calcium 5-pentyl picolinate as well as physiologically compatible salts thereof.

The production of the L-2-amino-3,3-dideutero-3-(3,4-dihydroxyphenyl) propionic acid is produced according to the method in Binns et al., J. Chem. Soc. (C), 1970, pages 1134-1138, where, among other things, the production of racemic 2-amino-3,3-dideutero-3-(3,4-dihydroxyphenyl) propionic acid is described. Dideutero-(3,4-dimethoxyphenyl) methane is produced starting from 3,4-dimethoxybenzoic acid ethyl ester by reaction with lithium aluminum deuteride. From this, 4-(chlorodideuteromethyl)-1,2-dimethoxybenzene is produced by reaction with thionyl chloride, and this reacts with the sodium salt of acetamidomalonic acid diethyl ester to form deuterated 3,4-dimethoxybenzylacetamidomalonic acid diethyl ester, which is converted to D,L-2-acetylamino-3,3-dideutero-3-(3,4-dimethoxyphenyl) propionic acid by treatment with ethanolic potassium hydroxide solution. The object according to the invention, which is to produce the L-enantiomer of the amino acid dideuterated in β,β-position could be accomplished by conducting a cleavage of the racemate at this site, which was analogous to the method disclosed in CH patent 59098. It was found also that L-2-acetylamino-3,3-dideutero-3-(3,4-dimethoxyphenyl) propionic acid can be very well isolated from the solution by forming crystals with (R)-(+)-1-phenylethylamine. The L-2-amino-3,3-dideutero-3-(3,4-dihydroxyphenyl) propionic acid according to the invention was then obtained from the L-2-acetylamino-3,3-dideutero-3-(3,4-dimethoxyphenyl) propionic acid by a clean cleavage of ether analogous to Jung et al., J. Org. Chem., Vol. 42, No. 23, 1977, pp. 3761-3764. The ester of the compound dideuterated in the β-position according to the invention was then produced from this amino acid by reaction with thionyl chloride and deuterated or undeuterated alcohol at low temperature.

It is of particular advantage here that the remaining D-2-acetylamino-3,3-dideutero-3-(3,4-dimethoxyphenyl) propionic acid could be isolated from the mother liquor of the racemate cleavage, and, after cleavage of the ether, could be used as an educt for the production of additional compounds according to the invention.

In addition, L-2-amino-3,3-dideutero-3-(3,4-dihydroxyphenyl) propionic acid serves as the educt for additional deuteration in the phenyl ring of the amino acid, which is performed by bringing the compound to react with $D_2O$ in the autoclave at 190° C., analogous to Vining et al., Journal of Labelled Compounds and Radiopharmaceuticals, Vol. XV1I1, No. 11, 1981, pp. 1683-1692. The L-2-amino-3,3-dideutero-3-(2,3,6-trideutero-4,5-dihydroxyphenyl) propionic acid that was obtained was then converted into the ester according to the invention, as described above. The stability of the ester obtained in the production or isolation of the ester was increased by the addition of an anti-oxidant, following the method disclosed in EP 610595.

The D-2-acetylamino-3,3-dideutero-3-(3,4-dimethoxyphenyl) propionic acid obtained by the above-described racemate cleavage was converted to the dihydroxy amino acid, analogously to the L compound, and was then used in order to produce the compounds according to the invention which are deuterated in the α-position, by performing a racemization with simultaneous deuteration analogous to Chen et al., Biotechnology Letters, Vol. 14, No. 4, 1992, pp. 269-274. For this purpose, D-2-acetylamino-3,3-dideutero-3-(3,4-dihydroxyphenyl) propionic acid was converted with benzaldehyde to deuterated acetic acid. The D- and L-2-acetylamino-3,3-dideutero-3-(3,4-dihydroxyphenyl) propionic acids deuterated in the α-position and present as the racemate were converted to the corresponding methyl esters and separated by means of alcalase; the L-2-acetylamino-3,3-dideutero-3-(3,4-dihydroxyphenyl) methyl propionate was enzymatically hydrolyzed to the carboxylic acid, while the methyl ester of the D-2-acetylamino-3,3-dideutero-3-(3,4-dihydroxyphenyl) propionic acid remained unreacted. The compounds were separated by means of HPLC.

The isolated L-2-acetylamino-2,3,3-trideutero-3-(3,4-dihydroxyphenyl) propionic acid was converted to the ester according to the invention and deuterated additionally at the phenyl ring corresponding to the method already explained above, in order to obtain the L-2-amino-2,3,3-trideutero-3-(2,3,6-trideutero-4,5-dihydroxyphenyl) propionic acid according to the invention, which was in turn converted to the ester according to the invention. The H/D exchange at the phenolic OH groups and at the amino group was conducted by multiple recrystallization from $D_2O$.

For the production of the physiologically compatible salts of the deuterated catecholamine derivatives according to the invention, the usual physiologically compatible inorganic and organic acids such as hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid can be used. Additional acids that can be used are described, for example, in Fortschritte der Arzneimittelforschung, Vol. 10, pp. 224-225, Birkhäuser Publishers, Basel and Stuttgart, 1966, and Journal of Pharmaceutical Sciences, Vol. 66, pp. 1-5 (1977).

The acid addition salts are usually obtained in a way known in and of itself by mixing the free base or solutions thereof with the corresponding acid or solutions thereof in an organic solvent, for example, a lower alcohol, such as methanol, ethanol, n-propanol or isopropanol or a lower ketone such as acetone, methyl ethyl ketone or methyl isobutyl ketone or an ether such as diethyl ether, tetrahydrofuran or dioxane. For better crystal precipitation, mixtures of the named solvents can also be used. In addition, physiologically compatible aqueous solutions of acid addition salts of the compounds used according to the invention can be produced therefrom in an aqueous acid solution.

The acid addition salts of the compounds according to the invention can be converted to the free base in a way known in and of itself, e.g., with alkalis or ion exchangers. Additional salts can be obtained from the free base by reaction with inorganic or organic acids, particularly those which are suitable for the formation of salts that can be employed therapeutically. These or also other salts of the new compound, such as, e.g., the picrate, may also serve for purification of the free base by converting the free base into a salt, separating this salt, and again releasing the base from the salt.

The subject of the present invention is also pharmaceuticals for oral, buccal, sublingual, nasal, rectal, subcutaneous, intravenous or intramuscular application as well as for inhalation, which, in addition to the usual vehicle and dilution agents, also contain a compound of general formula I or the acid addition salt thereof as an active ingredient.

The pharmaceuticals of the invention are produced, in the known way and with suitable dosage, with the usual solid or liquid vehicle substances or dilution agents and the usually used pharmaceutical-technical adjuvants corresponding to the desired type of application. The preferred preparations consist of a form of administration which is suitable for oral application. Such forms of administration include, for example, tablets, sucking tablets, film tablets, dragees, capsules, pills, powders, solutions, aerosols or suspensions or slow-release forms.

Of course, parenteral preparations such as injection solutions are also considered. In addition, suppositories, for example, have also been named as preparations. Corresponding tablets can be obtained, for example, by mixing the active substance with known adjuvants, for example, inert dilution agents such as dextrose, sugar, sorbitol, mannitol, polyvinylpyrrolidone, bursting agents such as corn starch or alginic acid, binders such as starches or gelantins, lubricants such as magnesium stearate or talc and/or agents for achieving a slow-release effect such as carboxypolymethylene, carboxymethylcellulose, cellulose acetate phthalate or polyvinyl acetate. The tablets may also consist of several layers.

Dragees can also be produced correspondingly, for controlled or delayed release forms of preparation, by coating the cores produced analogously to the tablets with agents commonly used in dragee coatings, for example, polyvinylpyrrolidone or shellac, gum arabic, talc, titanium dioxide or sugar. The dragee envelope may also consist of several layers, wherein the adjuvants mentioned above in the case of tablets can be used.

Solutions or suspensions containing the active substance used according to the invention may additionally contain agents that improve taste, such as saccharin, cyclamate or sugar, as well as, e.g., taste enhancers such as vanilla or orange extract. They may also contain suspension adjuvants such as sodium carboxymethylcellulose or preservatives such as p-hydroxybenzoate. Capsules containing active substances can be produced, for example, by mixing the active substance with an inert vehicle such as lactose or sorbitol and encapsulating this mixture in gelatin capsules. Suitable suppositories can be produced, for example, by mixing with vehicle agents provided therefor, such as neutral fats or polyethylene glycol or derivatives thereof.

The production of the pharmaceutical preparations according to the invention is known in and of itself, and is described in handbooks known to the person skilled in the art, for example, Hager's Handbuch ($5^{th}$ ed.) 2, 622-1045; List et al., Arzneiformenlehre [Instructions for Drug Forms], Stuttgart: Wiss. Verlagsges. 1985; Sucker et al., Pharmazeutische Technologie [Pharmaceutical Technology], Stuttgart: Thieme 1991; Ullmann's Enzyklopädie [Encyclopedia] (5th ed.) A 19, 241-271; Voigt, Pharmazeutische Technologie [Pharmaceutical Technology], Berlin: Ullstein Mosby 1995.

The following examples explain the invention:

EXAMPLE 1

Production of L-2-acetylamino-3,3-dideutero-3-(3,4-dimethoxyphenyl) propionic acid Analogously to the method for the undeuterated compound, 50 ml of acetone are added to 3.85 g of D,L-2-acetylamino-3,3-dideutero-3-(3,4-dimethoxyphenyl) propionic acid and the solution is heated. 0.865 g of (R)-(+)-1-phenylethylamine, dissolved in 5 ml of acetone, are added to this warm solution. The precipitated salt is again dissolved by addition of a small amount of methanol. The methanol is removed by repeated concentration of the reaction batch and the volume of the solution is brought to 50 ml by the addition of acetone. For crystallization of the salt formed from L-2-acetylamino-3,3-dideutero-3-(3,4-dimethoxyphenyl) propionic acid and (R)-(+)-1-phenylethylamine, the reaction batch is triturated with a glass rod and then after crystallization has begun, it is left to stand for 12 hours at room temperature. The crystals that form are separated, washed with cold acetone and diethyl ether and dried. 2.6 g of the salt are isolated.

The solvent is distilled off from the remaining mother liquor and the residue of D-2-acetylamino-3,3-dideutero-3-(3,4-dimethoxyphenyl) propionic acid is stored until further processing.

Yield: Melting point: 185-187° C.

$[\alpha]_D^{25}$=+56.4° (c=1 in methanol)

The salt is further processed without additional purification by dissolving 2.5 g in 15 ml of a 5% sodium hydroxide solution. The released (R)-(+)-1-phenylethylamine is removed from the solution by extraction with petroleum ether. After acidifying the aqueous phase with hydrochloric acid, a saturated sodium chloride solution is added and the solution is extracted with ethyl acetate. The organic phase is dried and the solvent is removed. The residue crystallizes overnight and L-2-acetylamino-3,3-dideutero-3-(3,4-dimethoxyphenyl) propionic acid is obtained. 1.48 g of product is obtained.

Yield: 86%

Melting point 135-137° C.

$[\alpha]_D^{25}$=+45.5° (c=1 in methanol)

| | | | |
|---|---|---|---|
| Theoretical: | C: 57.98% | H: 7.11% | N: 5.20% |
| Experimentally found: | C: 57.89% | H: 7.19% | N: 5.30% |

$^1$H-NMR (400 MHz, d6-DMSO): δ 6.48 (s, 1H); 6.60 (s, 1H); 6.54 (s, 1H); 7.8 (s, 1H); 4.60 (s, 1H); 3.70 (s, 6H); 2.20 (s, 3H).

EXAMPLE 2

Production of L-2-amino-3,3-dideutero-3-(3,4-dihydroxyphenyl) propionic acid 1.35 g of L-2-acetylamino-3,3-dideutero-3-(3,4-dimethoxyphenyl) propionic acid are dissolved in 17 ml of chloroform and then reacted with 26.3 ml of iodotrimethylsilane. The reaction batch is heated to 60° C. and the course of the reaction is followed by means of NMR. After 30 hours, the reaction is terminated, the batch is filtered and 15 ml of methanol are added to the filtrate. After 30 hours, the solvent is removed and 0.96 g of product is isolated.

Yield: 96%

Melting point 287-290° C. (decomp.)

$[\alpha]_D^{25}$=−11.7° (c=5.27 in 1 M HCl)

| | | | |
|---|---|---|---|
| Theoretical: | C: 54.27% | H: 6.58% | N: 7.03% |
| Experimentally found: | C: 54.10% | H: 6.60% | N: 7.11% |

$^1$H-NMR (400 MHz, d6-DMSO): δ 6.49 (s, 1H); 6.59 (s, 1H); 6.54 (s, 1H); 7.8 (s, 1H); 4.28 (s, 1H).

EXAMPLE 3

D-2-amino-3,3-dideutero-3-(3,4-dihydroxyphenyl) propionic acid

The D-2-acetylamino-3,3-dideutero-3-(3,4-dimethoxyphenyl) propionic acid obtained in Example 1 is converted to the D-2-amino-3,3-dideutero-3-(3,4-dihydroxyphenyl) propionic acid analogously to Example 2. 0.82 g of the deuterated dihydroxy amino acid is isolated from 1.2 g of the initial compound.

Yield: 92%

Melting point: 287-290° C. (decomp.)

$[\alpha]_D^{25}$=+11.5° (c=5.27 in 1 M HCl)

| | | | |
|---|---|---|---|
| Theoretical: | C: 54.27% | H: 6.58% | N: 7.03% |
| Experimentally found: | C: 54.31% | H: 6.55% | N: 7.10% |

$^{13}$C-NMR (200 MHz, d6-DMSO): δ 41.0 (quint); 62.50 (s); 116.20 (s); 117.30 (s); 121.70 (s); 133.80 (s); 141.40 (s); 144.40 (s); 176.40 (s).

EXAMPLE 4

Production of D,L-2-amino-2,3,3-trideutero-3-(3,4-dihydroxyphenyl) propionic acid 1.99 g of D-2-acetylamino-3,3-dideutero-3-(3,4-dihydroxyphenyl) propionic acid are reacted with 50 ml of singly deuterated acetic acid ($CH_3COOD$) and 0.2 ml of benzaldehyde is added. The reaction batch is rinsed with nitrogen and then heated to reflux for one hour. After the end of the reaction time, the solvent is removed and the residue is reacted with 20 ml of ethanol. The precipitated solid is filtered off and 1.74 g of D,L-2-amino-2,3,3-trideutero-3-(3,4-dihydroxyphenyl) propionic acid is isolated.

Yield: 87%

Melting point: 287-290° C. (decomp.)

| | | | |
|---|---|---|---|
| Theoretical: | C: 53.99% | H: 7.05% | N: 7.00% |
| Experientally found: | C: 53.90% | H: 7.12% | N: 7.04% |

$^1$H-NMR (400 MHz, d6-DMSO): δ 6.47 (s, 1H); 6.59 (s, 1H); 6.52 (s, 1H); 7.8 (s, 1H).

EXAMPLE 5

Production of D,L-2-amino-2,3,3-trideutero-3-(3,4-dihydroxyphenyl) methyl propionate 2 g of D,L-2-amino-2,3,3-trideutero-3-(3,4-dihydroxyphenyl) proponic acid in 30 ml of methanol are cooled to −10° C. and reacted dropwise with 1 ml of thionyl chloride. The reaction batch is then heated to 40° C. for 15 hours. The volatile substances in the reaction batch are eliminated in vacuum and 10 ml of water and 15 ml of a solution of 0.8 g of sodium hydrogen carbonate, 1 g of sodium sulfate and 1 mg of ascorbic acid are added. The pH of the solution is adjusted to a value of 7 by addition of a dilute sodium hydroxide solution. The product is transferred to the organic phase by extraction with oxygen-free ethyl aectate, which contains 0.01% 2,6-di-tert-butyl-4-methoxyphenol. The organic phase is dried and then the solvent is distilled off. 50 ml of oxygen-free diethyl ether are added to the residue and after this material is left to stand overnight, the D,L-2-amino-2,3,3-trideutero-3-(3,4-dihydroxyphenyl) methyl propionate precipitates. After recrystallization from an oxygen-free methanol/diethyl ether mixture which is combined with 2,6-di-tert-butyl-4-methoxyphenol, 1.8 g of product is isolated.

Yield: 85%

| | | | |
|---|---|---|---|
| Theoretical: | C: 56.06% | H: 7.53% | N: 6.54% |
| Experientally found: | C: 56.20% | H: 7.48% | N: 6.55% |

$^1$H-NMR (400 MHz, d6-DMSO): δ 6.48 (s, 1H); 6.59 (s, 1H); 6.54 (s, 1H); 7.8 (s, 1H); 3.80 (s, 3H).

EXAMPLE 6

L-2-amino-2,3,3-trideutero-3-(3,4-dihydroxyphenyl) propionic acid 1.07 g of D,L-2-amino-2,3,3-trideutero-3-(3,4-dihydroxyphenyl) methyl propionate is dissolved in 30 ml of a 0.2-molar sodium bicarbonate solution (pH 8.2). 200 μl of alcalase are added and the pH of the solution is kept at this value by means of a carbonate-bicarbonate buffer. The course of the reaction is monitored by means of HPLC and the reaction is terminated by the addition of hydrochloric acid when the concentration of the propionate ester has been reduced to one-half. The trideuterated amino acid contained in the solution is separated from the trideuterated methyl ester chromatographically with the use of the solvent system of acetonitrile/0.1% aqueous trifluoroacetic acid (15:85) and 1.04 g of L-2-amino-2,3,3-trideutero-3-(3,4-dihydroxyphenyl) propionic acid is isolated.

Yield: 97%

Melting point: 287-290° C. (decomp.)

$[\alpha]_D^{25}$=−11.6° (c=5.27 in 1 M HCl)

| | | | |
|---|---|---|---|
| [Theoretical]: | C: 53.99% | H: 7.05% | N: 7.00% |
| Experientally found: | C: 53.83% | H: 7.12% | N: 6.91% |

$^{13}$C-NMR (200 MHz, d6-DMSO): δ 41.0 (quint); 62.40 (trip.); 116.20 (s); 117.30 (s); 121.70 (s); 133.80 (s); 141.40 (s); 144.40 (s); 176.40 (s).

EXAMPLE 7

Production of L-2-amino-2,3,3-trideutero-3-(2,3,6-trideutero-4-dihydroxyphenyl) propionic acid 0.2 g of L-2-amino-2,3,3-trideutero-3-(3,4-dihydroxyphenyl) propionic acid are reacted with 10 ml of $D_2O$ in an autoclave. The autoclave is evacuated and heated to a temperature of 190° C. for 24 hours. After the reaction has terminated, the solvent is removed, the residue is mixed with ethyl acetate and the solvent is distilled off in vacuum. The residue is washed with cold acetone and 0.17 g of product is isolated.

Yield: 84%

Melting point: 287-290° C. (decomp.)

$[\alpha]_D^{25}$=−11.5° (c=5.27 in 1 M HCl)

| | | | |
|---|---|---|---|
| [Theoretical]: | C: 53.19% | H: 8.43% | N: 6.89% |
| Experientally found: | C: 53.30% | H: 8.31% | N: 7.00% |

$^{13}$C-NMR (200 MHz, d6-DMSO): 41.0 (quint); 62.40 (t); 116.30 (t); 117.20 (t); 121.70 (t); 133.80 (s); 141.30 (s); 144.40 (s); 176.40 (s).

The invention claimed is:

[1. Deuterated catecholamine derivatives of the general formula I

Formula I

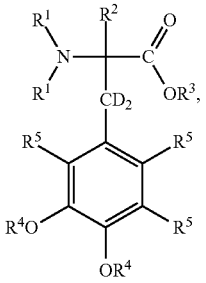

wherein $R^1$ is H or D, R2 indicates D, $R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is H or hhD.]

[2. Deuterated catecholamine derivatives of the general formula I

Formula I

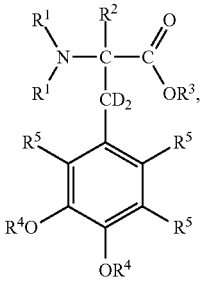

wherein $R^1$ is H or D, $R^2$ indicates D, $R^3$ is D, $C_1$ to $C_6$-alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is H or D.]

[3. Deuterated catecholamine derivatives of the general formula I

Formula I

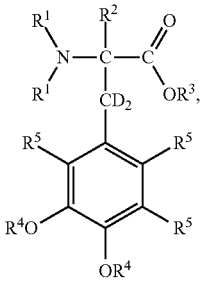

wherein $R^1$ is H or D, $R^2$ indicates D, $R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl, $R^4$ indicates H or D and $R^5$ is H or D.]

[4. Deuterated catecholamine derivatives of the general formula I

Formula I

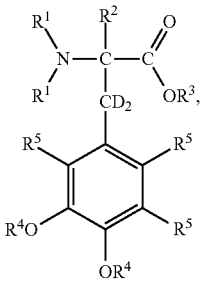

wherein $R^1$ is H or D, $R^2$ indicates D, $R^3$ is $C_1$ to $C_6$-alkyl or $C_5$ to $C_6$-cycloalkyl, $R^4$ indicates H or D and $R^5$ is H or D.]

[5. Deuterated catecholamine derivatives of the general formula I

Formula I

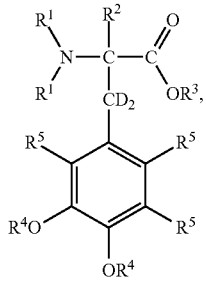

wherein $R^1$ is H or D, $R^2$ indicates D, $R^3$ is methyl, $R^4$ indicates H or D and $R^5$ is H or D.]

[6. Deuterated catecholamine derivatives of the general formula I

Formula I

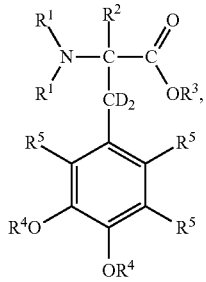

wherein $R^1$ is H or D, $R^2$ indicates D, $R^3$ is ethyl, $R^4$ indicates H or D and $R^5$ is H or D.]

[7. Deuterated catecholamine derivatives of the general formula I

Formula I

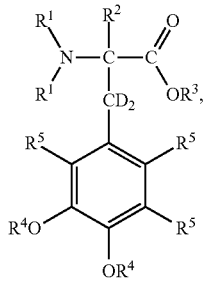

wherein $R^1$ is H or D, $R^2$ indicates D, $R^3$ is perdeuteroethyl, $R^4$ indicates H or D and $R^5$ is H or D.]

[8. Deuterated catecholamine derivatives of the general formula I

Formula I

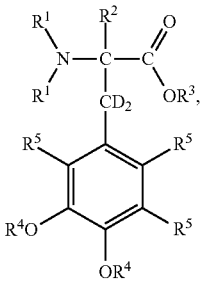

wherein $R^1$ is H or D, R2 indicates D, $R^3$ is perdeuteroethyl, $R^4$ indicates H or D and $R^5$ is H or D.]

[9. Deuterated catecholamine derivatives of the general formula I

Formula I

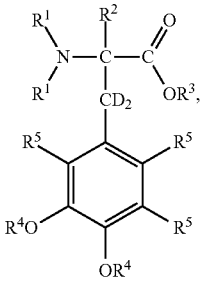

wherein $R^1$ is H or D, $R^2$ indicates D, $R^3$ is perdeuteroethyl, $R^4$ indicates D and $R^5$ is H or D.]

10. A method for [the treatment of] *treating a* dopamine deficiency [diseases or diseases] *disease, treating a disease* which [are] *is* based on disrupted tyrosine transport or disrupted tyrosine decarboxylase, [or] *treating* Parkinson's disease, *treating* restless leg syndrome, *treating* dystonia, [for] inhibiting prolactin secretion, [for] stimulating the release of growth hormone, [for the treatment of] *treating* neurological symptoms of chronic manganese [intoxications] *intoxication*, [of] *treating* amyotrophic lateral sclerosis [and of], *or treating* multiple system atrophy, [said method] comprising administering to a patient in need thereof an effective amount of [a compound of general formula I Formula I

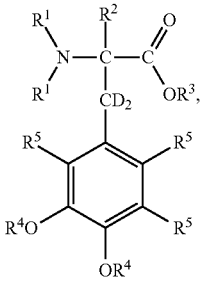

wherein $R^1$ is H or D, $R^2$ indicates D, $R^3$ is H, D, $C_1$-$C_6$-alkyl or $C_5$ to $C_6$-cycloalkyl, deuterated $C_1$ to $C_6$-alkyl or $C_5$ to $C_6$-cycloalkyl, $R^4$ indicates H or D and $R^5$ is H or D, and wherein the compound is selected from the group consisting of,]

L-2-amino-2,3,3-trideutero-3-(3,4-dihydroxyphenyl)propionic acid[;],

[L-2-amino-2,3,3-trideutero-3-(3,4-dihydroxyphenyl) methyl propionate;

L-2-amino-2,3,3-trideutero-3-(3,4-dihydroxyphenyl) ethyl propionate;

L-2-amino-2,3,3-trideutero-3-(3,4-dihydroxyphenyl)cyclohexyl propionate;

L-2-amino-2,3,3-trideutero-3-(3,4-dihydroxyphenyl)perdeuteromethyl propionate;

L-2-amino-2,3,3-trideutero-3-(3,4-dihydroxyphenyl)perdeuteroethyl propionate;

L-2-amino-2,3,3-trideutero-3-(3,4-dihydroxyphenyl)perdeuterocyclohexyl propionate;

L-2-amino-2,3,3-trideutero-3-(2,3,6-trideutero-4,5-dihydroxyphenyl)propionic acid;

L-2-amino-2,3,3-trideutero-3-(2,3,6-trideutero-4,5-dihydroxyphenyl)methyl propionate;

L-2-amino-2,3,3-trideutero-3-(2,3,6-trideutero-4,5-dihydroxyphenyl)ethyl propionate;

L-2-amino-2,3,3-trideutero-3-(2,3,6-trideutero-4,5-dihydroxyphenyl)cyclohexyl propionate;

L-2-amino-2,3,3-trideutero-3-(2,3,6-trideutero-4,5-dihydroxyphenyl)perdeuteromethyl propionate;

L-2-amino-2,3,3-trideutero-3-(2,3,6-trideutero-4,5-dihydroxyphenyl)perdeuteroethyl propionate;

L-2-amino-2,3,3-trideutero-3-(2,3,6-trideutero-4,5-dihydroxyphenyl)perdeuterocyclohexyl propionate;

L-2-amino-2,3,3-trideutero-3-(2,3,6-trideutero-4,5-dideuteroxyphenyl)perdeuterocyclohexyl propionate; and, as well as] *or a* physiologically compatible [salts] *salt* thereof.

11. The method of claim 10, wherein the [compound as well as] *L-2-amino-2,3,3-trideutero-3-(3,4-dihydroxyphenyl)propionic acid or the* physiologically compatible [salts] *salt* thereof is administered in combination with an enzyme inhibitor or several enzyme inhibitors.

12. The method [as claimed in] *of* claim 11, wherein the enzyme inhibitor or the *several* enzyme inhibitors [involve] are decarboxylase inhibitors and/or catechol-O-methyltransferase inhibitors and/or monoamine oxidase inhibitors and/or β-hydroxylase inhibitors.

13. The method [as claimed in] *of* claim 12, wherein the decarboxylase inhibitor is [selected from the group consisting of] D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl)hydrazide, glycine 2-(2,3,4-trihydroxybenzyl) hydrazide [and], *or* L-tyrosine 2-(2,3,4-trihydroxybenzyl) hydrazide [as well as], *or a* physiologically compatible [salts] *salt* thereof.

14. The method [as claimed in] *of* claim 12, wherein the catechol-O-methyltransferase inhibitor is [selected from] entacapone [and] *or* cabergoline [as well as] *or a* physiologically compatible [salts] *salt* thereof.

15. The method [as claimed in] *of* claim 12, wherein the monoamine oxidase inhibitor is [selected from the group consisting of] selegiline, moclobemide [and], *or* tranylcypromine [as well as] *or a* physiologically compatible [salts] *salt* thereof.

16. The method [as claimed in] *of* claim 12, wherein the β-hydroxylase inhibitor is [selected from] calcium 5-butyl picolinate [and] *or* calcium 5-pentyl picolinate [as well as] *or a* physiologically compatible [salts] *salt* thereof.

[17. A method for the production of pharmaceuticals for treatment of dopamine deficiency diseases or diseases which are based on disrupted tyrosine transport or disrupted tyrosine decarboxylase, or Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy, said method comprising the steps of providing a compound of general formula I Formula I

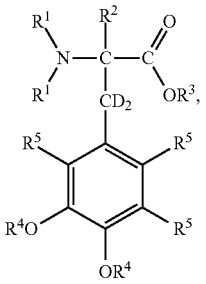

wherein $R^1$ is H or D, $R^2$ indicates D, $R^3$ is H, D, $C_1$-$C_6$ alkyl or $C_5$ to $C_6$-cycloalkyl, deuterated $C_1$ to $C_6$-alkyl or $C_5$ to $C_6$-cycloalkyl, $R^4$ indicates H or D and $R^5$ is H or D, and wherein the compound is selected from the group consisting of L-2-amino-2,3,3-trideutero-3-(3,4-dihydroxyphenyl)propionic acid;

L-2-amino-2,3,3-trideutero-3-(3,4-dihydroxyphenyl) methyl propionate;

L-2-amino-2,3,3-trideutero-3-(3,4-dihydroxyphenyl) ethyl propionate;

L-2-amino-2,3,3-trideutero-3-(3,4-dihydroxyphenyl)cyclohexyl propionate;

L-2-amino-2,3,3-trideutero-3-(3,4-dihydroxyphenyl)perdeuteromethyl propionate;

L-2-amino-2,3,3-trideutero-3-(3,4-dihydroxyphenyl)perdeuteroethyl propionate;

L-2-amino-2,3,3-trideutero-3-(3,4-dihydroxyphenyl)perdeuterocyclohexyl propionate;

L-2-amino-2,3,3-trideutero-3-(2,3,6-trideutero-4,5-dihydroxyphenyl)propionic acid;

L-2-amino-2,3,3-trideutero-3-(2,3,6-trideutero-4,5-dihydroxyphenyl)methyl propionate;

L-2-amino-2,3,3-trideutero-3-(2,3,6-trideutero-4,5-dihydroxyphenyl)ethyl propionate;

L-2-amino-2,3,3-trideutero-3-(2,3,6-trideutero-4,5-dihydroxyphenyl)cyclohexyl propionate;

L-2-amino-2,3,3-trideutero-3-(2,3,6-trideutero-4,5-dihydroxyphenyl)perdeuteromethyl propionate;

L-2-amino-2,3,3-trideutero-3-(2,3,6-trideutero-4,5-dihydroxyphenyl)perdeuteroethyl propionate;

L-2-amino-2,3,3-trideutero-3-(2,3,6-trideutero-4,5-dihydroxyphenyl)perdeuterocyclohexyl propionate;

L-2-amino-2,3,3-trideutero-3-(2,3,6-trideutero-4,5-dideuteroxyphenyl)perdeuterocyclohexyl propionate; and as well as physiologically compatible salts thereof and combining said compound and physiologically compatible salts with pharmaceutically compatible adjuvants and additives.]

18. A pharmaceutical composition [for the treatment of Parkinson's disease, of restless leg syndrome, of dystonia, for inhibiting prolactin secretion, for stimulating the release of growth hormone, for the treatment of neurological symptoms of chronic manganese intoxications, of amyotrophic lateral sclerosis and of multiple system atrophy, which pharmaceutical composition comprises a compound of general formula I Formula I

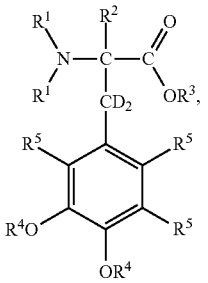

wherein $R^1$ is H or D, $R^2$ indicates D, $R^3$ is H, D, $C_1$-$C_6$ alkyl or $C_5$ to $C_6$-cycloalkyl, deuterated $C_1$ to $C_6$-alkyl or $C_5$ to $C_6$-cycloalkyl, $R^4$ indicates H or D and $R^5$ is H or D, and wherein the compound is selected from the group consisting of] *comprising*

L-2-amino-2,3,3-trideutero-3-(3,4-dihydroxyphenyl)propionic acid[;

L-2-amino-2,3,3-trideutero-3-(3,4-dihydroxyphenyl) methyl propionate;

L-2-amino-2,3,3-trideutero-3-(3,4-dihydroxyphenyl) ethyl propionate;

L-2-amino-2,3,3-trideutero-3-(3,4-dihydroxyphenyl)cyclohexyl propionate;

L-2-amino-2,3,3-trideutero-3-(3,4-dihydroxyphenyl)perdeuteromethyl propionate;

L-2-amino-2,3,3-trideutero-3-(3,4-dihydroxyphenyl)perdeuteroethyl propionate;

L-2-amino-2,3,3-trideutero-3-(3,4-dihydroxyphenyl)perdeuterocyclohexyl propionate;

L-2-amino-2,3,3-trideutero-3-(2,3,6-trideutero-4,5-dihydroxyphenyl)propionic acid;

L-2-amino-2,3,3-trideutero-3-(2,3,6-trideutero-4,5-dihydroxyphenyl)methyl propionate;

L-2-amino-2,3,3-trideutero-3-(2,3,6-trideutero-4,5-dihydroxyphenyl)ethyl propionate;

L-2-amino-2,3,3-trideutero-3-(2,3,6-trideutero-4,5-dihydroxyphenyl)cyclohexyl propionate;

L-2-amino-2,3,3-trideutero-3-(2,3,6-trideutero-4,5-dihydroxyphenyl)perdeuteromethyl propionate;

L-2-amino-2,3,3-trideutero-3-(2,3,6-trideutero-4,5-dihydroxyphenyl)perdeuteroethyl propionate;

L-2-amino-2,3,3-trideutero-3-(2,3,6-trideutero-4,5-dihydroxyphenyl)perdeuterocyclohexyl propionate;

L-2-amino-2,3,3-trideutero-3-(2,3,6-trideutero-4,5-dideuteroxyphenyl)perdeuterocyclohexyl propionate; and as well as] *or a* physiologically compatible [salts] *salt* thereof, [in addition to] *for treating Parkinson's disease, treating restless leg syndrome, treating dystonia, inhibiting prolactin secretion, stimulating the release of growth hormone, treating neurological symptoms of chronic manganese intoxication, treating amyotrophic lateral sclerosis, or treating multiple system atrophy, and a* pharmaceutically compatible [adjuvants and additives] *adjuvant or additive.*

19. The pharmaceutical composition of claim 18 further comprising one or more enzyme inhibitors.

[20. The pharmaceutical composition according to claim 19, further characterized in that the enzyme inhibitor or the enzyme inhibitors involve decarboxylase inhibitors and/or catechol-O-methyltransferase inhibitors and/or monoamine oxidase inhibitors and/or β-hydroxylase inhibitors.]

[21. The pharmaceutical composition according to claim 19, further characterized in that the decarboxylase inhibitor is selected from the group consisting of D,L-serine 2-(2,3,4-trihydroxybenzyl)hydrazide(benserazide), (−)-L-α-hydrazino-3,4-dihydroxy-α-methylhydrocinnamic acid(carbidopa), L-serine 2-(2,3,4-trihydroxybenzyl)hydrazide, glycine 2-(2,3,4-trihydroxybenzyl)hydrazide and L-tyrosine 2-(2,3,4-trihydroxybenzyl)hydrazide as well as physiologically compatible salts thereof.]

[22. The pharmaceutical composition according to claim 19, further characterized in that the catechol-O-methyltransferase inhibitor is selected from entacapone and cabergoline as well as physiologically compatible salts thereof.]

[23. The pharmaceutical composition according to claim 19, further characterized in that the monoamine oxidase inhibitor is selected from the group consisting of selegiline, moclobemide and tranylcypromine as well as physiologically compatible salts thereof.]

[24. The pharmaceutical composition according to claim 19, further characterized in that the β-hydroxylase inhibitor is selected from calcium 5-butyl picolinate and calcium 5-pentyl picolinate as well as physiologically compatible salts thereof.]

*25. The method of claim 10 for treating Parkinson's disease.*

*26. The method of claim 10 for treating restless leg syndrome.*

*27. The method of claim 10 for treating dystonia.*

*28. The method of claim 10 for treating neurological symptoms of chronic manganese intoxication.*

*29. The method of claim 10 for treating amyotrophic lateral sclerosis.*

*30. The method of claim 10 for treating multiple system atrophy.*

*31. The pharmaceutical composition of claim 18, for treating Parkinson's disease.*

*32. The pharmaceutical composition as recited in claim 18, for treating restless leg syndrome.*

*33. The pharmaceutical composition of claim 18, for treating dystonia.*

*34. The pharmaceutical composition of claim 18, for treating neurological symptoms of chronic manganese intoxication.*

*35. The pharmaceutical composition of claim 18, for treating amyotrophic lateral sclerosis.*

*36. The pharmaceutical composition of claim 18, for treating multiple system atrophy.*

* * * * *